(12) United States Patent
Thompson

(10) Patent No.: US 9,788,976 B1
(45) Date of Patent: Oct. 17, 2017

(54) SECURING APPARATUS FOR A PROSTHETIC LEG

(71) Applicant: Delbert Thompson, Cana, VA (US)

(72) Inventor: Delbert Thompson, Cana, VA (US)

( * ) Notice: Subject to any disclaimer, the term of this patent is extended or adjusted under 35 U.S.C. 154(b) by 0 days.

(21) Appl. No.: 15/079,701

(22) Filed: Mar. 24, 2016

(51) Int. Cl.
*A61F 2/78* (2006.01)
*A41F 18/00* (2006.01)
*A61F 2/50* (2006.01)
*A41F 19/00* (2006.01)

(52) U.S. Cl.
CPC ................ *A61F 2/78* (2013.01); *A41F 18/00* (2013.01); *A41F 19/00* (2013.01); *A61F 2002/5072* (2013.01); *A61F 2002/5083* (2013.01); *A61F 2002/7862* (2013.01); *A61F 2002/7875* (2013.01); *A61F 2002/7881* (2013.01)

(58) Field of Classification Search
CPC ...... A61F 2002/7862; A61F 2002/7881; A41F 17/04; A41F 18/00; A41F 19/00
USPC ...................................... 623/31, 32
See application file for complete search history.

(56) References Cited

U.S. PATENT DOCUMENTS

| | | | | |
|---|---|---|---|---|
| 1,801,562 A | * | 4/1931 | Luft | .......................... A41D 1/06 2/128 |
| D677,842 S | | 3/2013 | Kalbach | |
| 8,746,149 B2 | | 6/2014 | Elhard | |
| 8,858,408 B2 | | 10/2014 | DeMeo | |
| 2017/0095373 A1 | * | 4/2017 | Dellacqua | ......... A61F 13/00038 |

FOREIGN PATENT DOCUMENTS

EP     0 288 663 A1 * 11/1988 ............. A41F 19/00

* cited by examiner

*Primary Examiner* — David H Willse
(74) *Attorney, Agent, or Firm* — Stevenson IP, LLC

(57) ABSTRACT

A securing apparatus for a prosthetic leg including a belt strap, a pair of hook and loop fasteners disposed on the belt strap, and a pair of top attachment loops attached to the belt strap. A sled-shaped support attachment includes a flattened base portion, a pair of support extensions, and a pair of bottom attachment loops. Each of a right ratchet strap and a left ratchet strap of a pair of ratchet straps has an upper spring-loaded clip and a lower spring-loaded clip. The upper spring-loaded clip of each of the right ratchet strap and the left ratchet strap is attachable to the right top attachment loop and the left top attachment loop, respectively. The lower spring-loaded clip of each of the right ratchet strap and the left ratchet strap is attachable to a right bottom attachment loop and a left bottom attachment loop, respectively, of the support attachment.

6 Claims, 7 Drawing Sheets

SECURING APPARATUS FOR A PROSTHETIC LEG

BACKGROUND OF THE INVENTION

Various types of prosthetic leg accessories are known in the prior art. However, what has been needed is a securing apparatus for a prosthetic leg including a belt strap, a pair of hook and loop fasteners disposed on the belt strap, and a pair of top attachment loops attached to the belt strap. What has been further needed is a sled-shaped support attachment that includes a flattened base portion, a pair of support extensions, and a pair of bottom attachment loops. Lastly, what has been needed is for each of a right ratchet strap and a left ratchet strap of a pair of ratchet straps to have an upper spring-loaded clip and a lower spring-loaded clip. The upper spring-loaded clip of each of the right ratchet strap and the left ratchet strap is attachable to the right top attachment loop and the left top attachment loop, respectively. The lower spring-loaded clip of each of the right ratchet strap and the left ratchet strap is attachable to a right bottom attachment loop and a left bottom attachment loop, respectively, of the support attachment. The support attachment selectively supports a foot portion of a prosthetic leg between the pair of support extensions when the pair of ratchet straps has attached the support attachment to the belt strap. The securing apparatus for a prosthetic leg thus provides additional securement to a user's prosthetic leg while the user is engaged in any type of particularly extreme activity including, but not limited to, riding amusement park rides and sky diving.

FIELD OF THE INVENTION

The present invention relates to prosthetic leg accessories, and more particularly, to a securing apparatus for a prosthetic leg.

SUMMARY OF THE INVENTION

The general purpose of the present securing apparatus for a prosthetic leg, described subsequently in greater detail, is to provide a securing apparatus for a prosthetic leg which has many novel features that result in a securing apparatus for a prosthetic leg which is not anticipated, rendered obvious, suggested, or even implied by prior art, either alone or in combination thereof.

To accomplish this, the present securing apparatus for a prosthetic leg includes a belt strap having a right end, a left end, an interior surface, and an exterior surface. A pair of hook and loop fasteners includes a hook fastener and a loop fastener, with each of the hook fastener and the loop fastener disposed on the interior surface of the belt strap proximal the right end and the exterior surface of the belt strap proximal the left end, respectively. The pair of hook and loop fasteners is configured to selectively secure the right end to the left end around a waist of a user. A pair of top attachment loops includes a right top attachment loop and a left top attachment loop, with each of the right top attachment loop and the left top attachment loop having a pair of top ends attached to the exterior surface of the belt strap proximal the right end and the left end, respectively.

The securing apparatus for a prosthetic leg further includes a sled-shaped support attachment. The support attachment includes a substantially rectangular flattened base portion, a pair of substantially trapezoidal support extensions, and a pair of bottom attachment loops. The base portion has a linear back edge, a right edge, a left edge, an upper surface, a lower surface, and an upwardly disposed convexly curved front area. A gripping member is optionally disposed on the upper surface of the base portion of the support attachment. Both the curved front area and the gripping member assist in securing a foot portion of a prosthetic leg between the pair of support extensions. The pair of substantially trapezoidal support extensions includes a right support extension and a left support extension, with each of the right support extension and the left support extension having a top surface, an exterior side surface, and a bottom surface medially disposed on the upper surface of the base portion adjacent to the right edge and the left edge, respectively. Each of the pair of support extensions is perpendicularly disposed to the base portion. The pair of bottom attachment loops includes a right bottom attachment loop and a left bottom attachment loop, with each of the right bottom attachment loop and the left bottom attachment loop having a pair of bottom ends attached to the exterior side surface of each of the right support extension and the left support extension, respectively, proximal the top surface.

Each of a right ratchet strap and a left ratchet strap of a pair of ratchet straps has an upper end, a lower end, a rearward facing upper spring-loaded clip attached to the upper end, and a frontward facing lower spring-loaded clip attached to the lower end. The upper spring-loaded clip of each of the right ratchet strap and the left ratchet strap is removably attachable to the right top attachment loop and the left top attachment loop, respectively. The lower spring-loaded clip of each of the right ratchet strap and the left ratchet strap is removably attachable to the right bottom attachment loop and the left bottom attachment loop, respectively, of the support attachment. Lastly, an expandable strap has a right loop and a left loop, with each of the right loop and the left loop slidably disposed around the right ratchet strap and the left ratchet strap, respectively, proximal the lower end. The support attachment selectively supports the foot portion of the prosthetic leg between the pair of support extensions when the pair of ratchet straps attaches the support attachment to the belt strap. Each of the pair of ratchet straps ensures that the length of the apparatus is adjustable depending on the height of a user.

The securing apparatus for a prosthetic leg optionally includes a second top attachment loop having a pair of second ends attached to the exterior surface of the belt strap proximal the right top attachment loop. The right top attachment loop is collinearly disposed between the hook fastener and the second top attachment loop. The optional second top attachment loop allows a double amputee to also make use of the apparatus by providing an additional means of attachment for a ratchet strap. The securing apparatus for a prosthetic leg additionally optionally includes a support strap having a securing mechanism. The securing mechanism selectively secures the support strap around the upper leg of the user and the pair of ratchet straps. The support strap helps to ensure that the apparatus remains in place when worn by the user.

Thus has been broadly outlined the more important features of the present securing apparatus for a prosthetic leg so that the detailed description thereof that follows may be better understood and in order that the present contribution to the art may be better appreciated.

BRIEF DESCRIPTION OF THE DRAWINGS

Figures

DETAILED DESCRIPTION OF THE DRAWINGS

Figure 1:
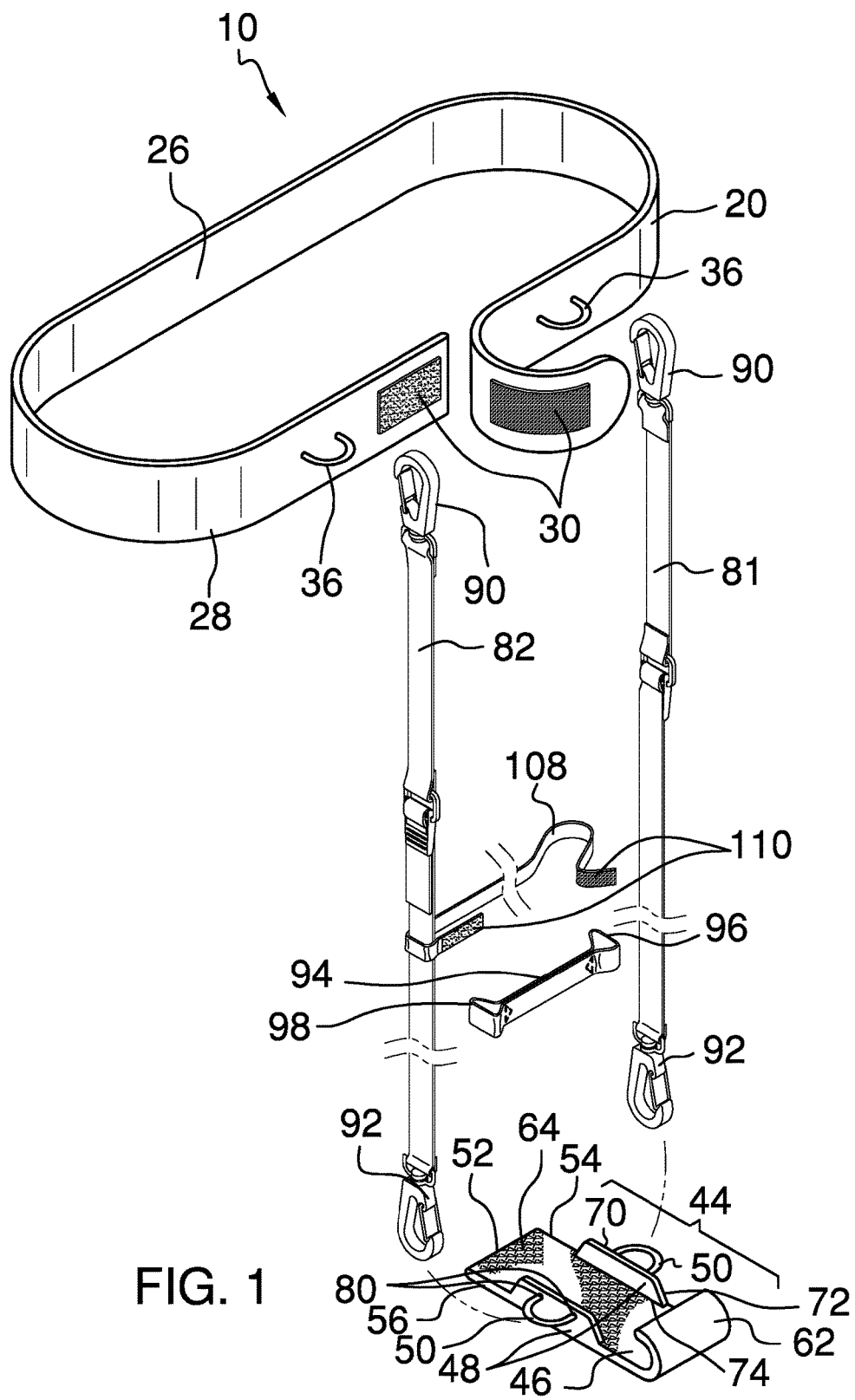
FIG. 1 is a front isometric view.
Figure 2:
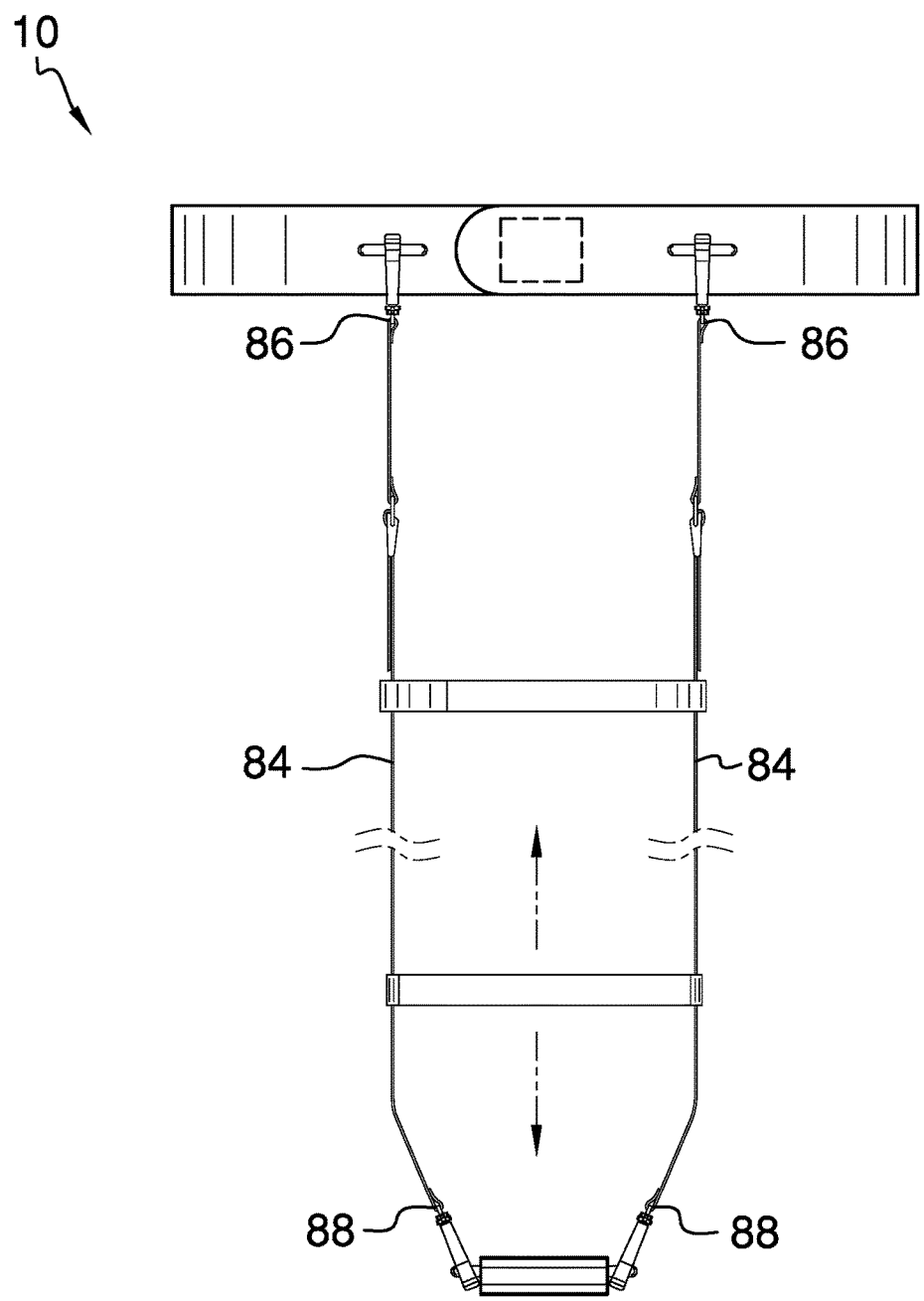
FIG. 2 is a front elevation view.
Figure 3:
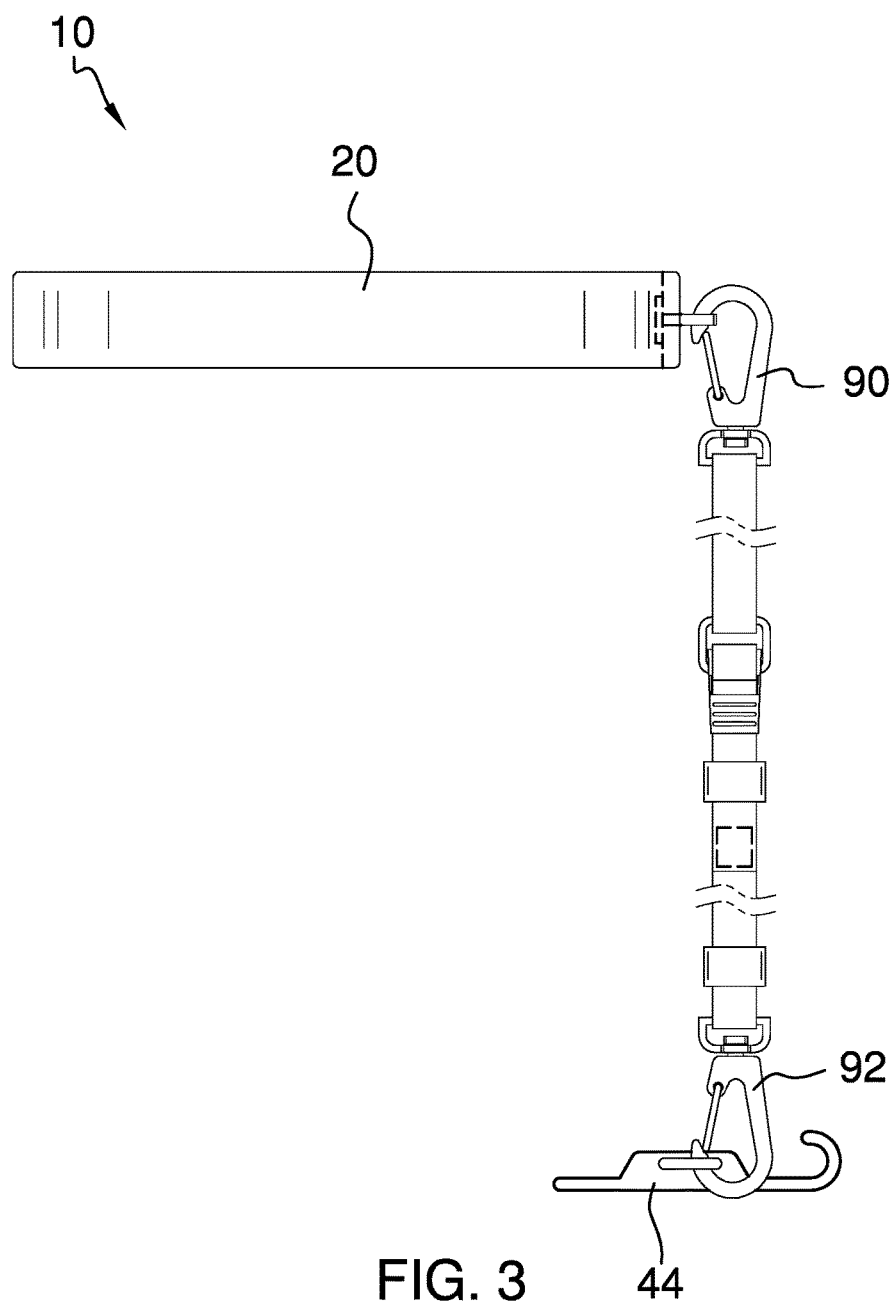
FIG. 3 is a side elevation view.
Figure 4:
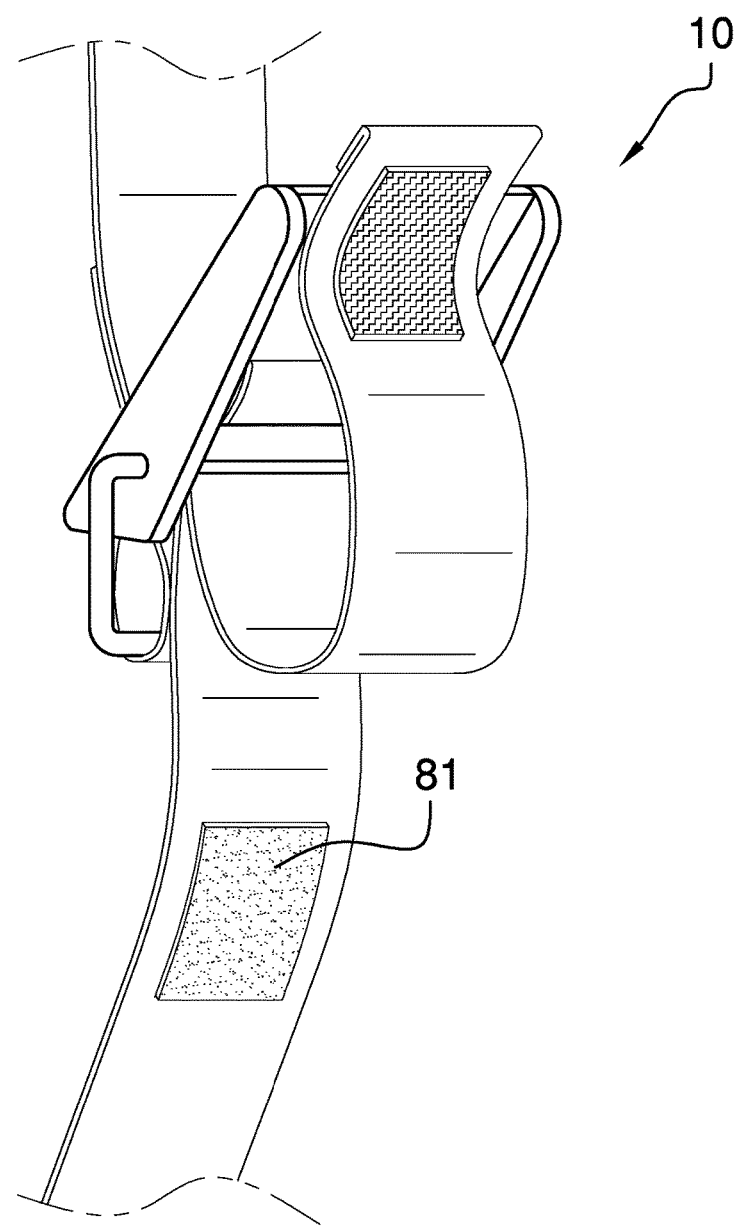
FIG. 4 is a detail view showing a ratchet strap.
Figure 5:
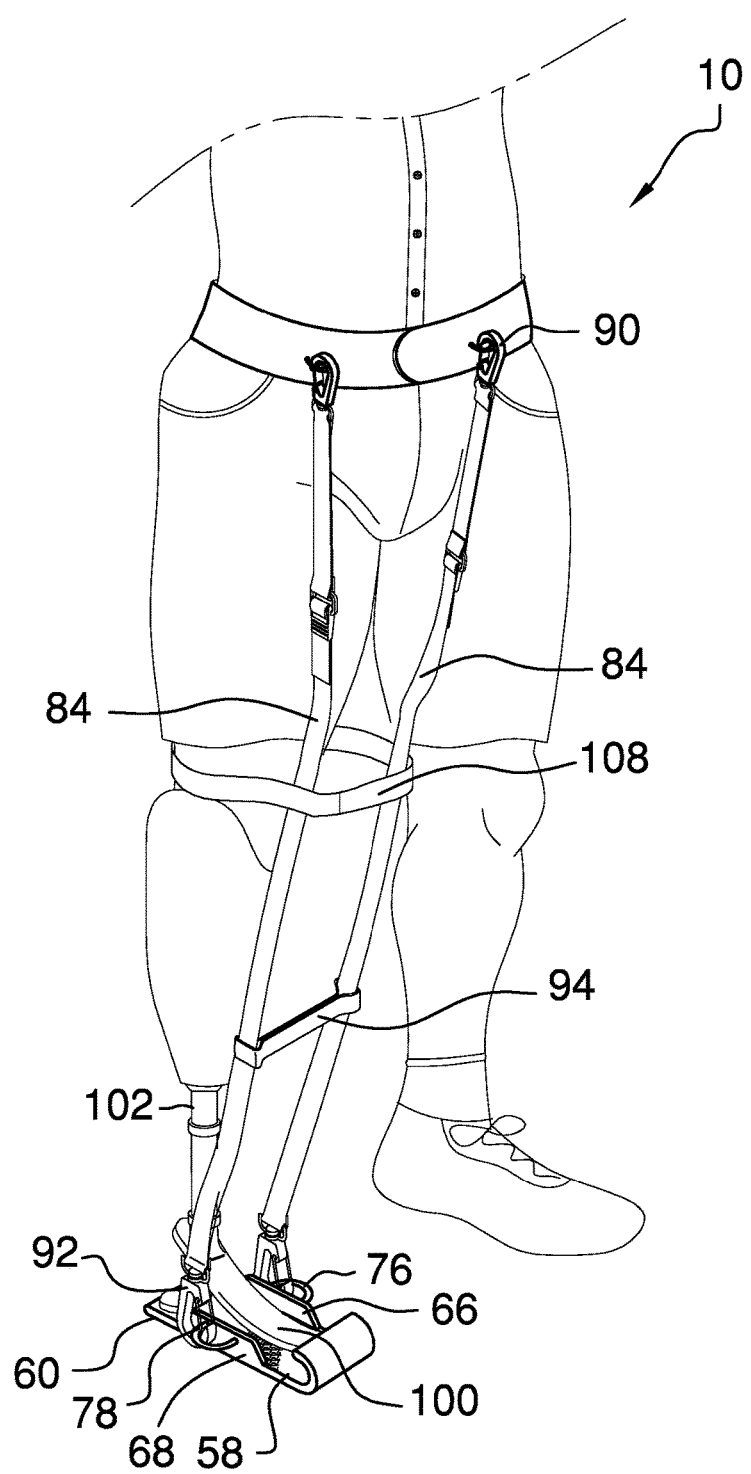
FIG. 5 is an in use view showing a support strap.
Figure 6:
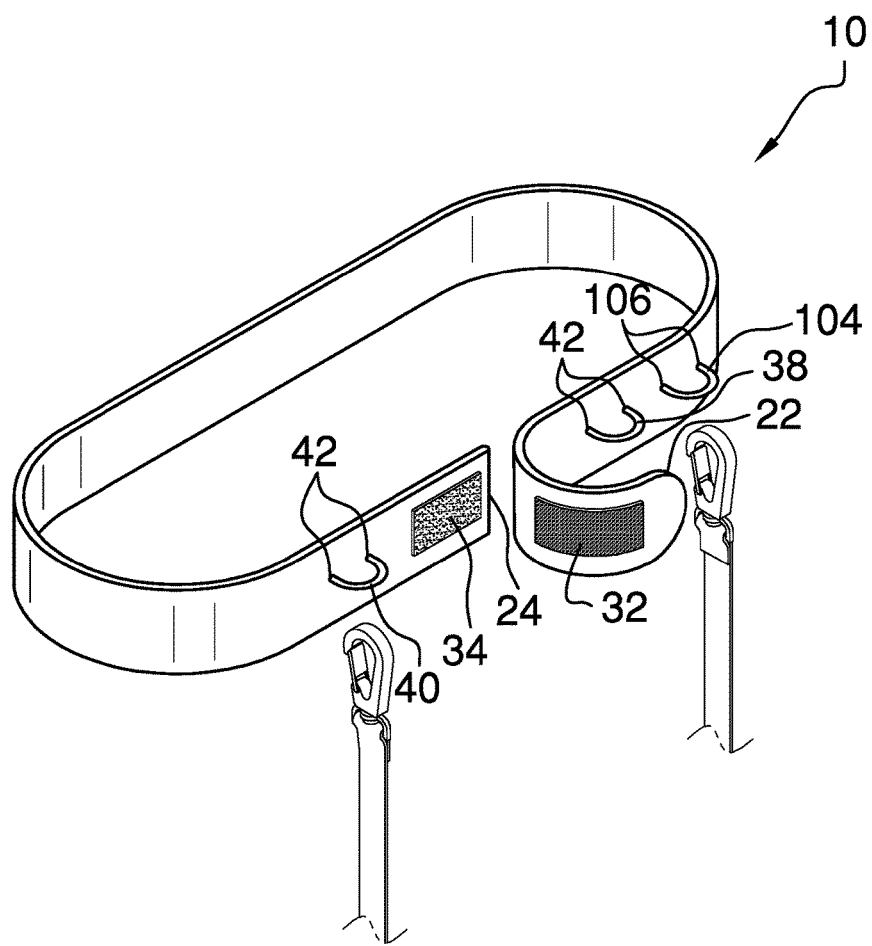
FIG. 6 is a detail view.
Figure 7:
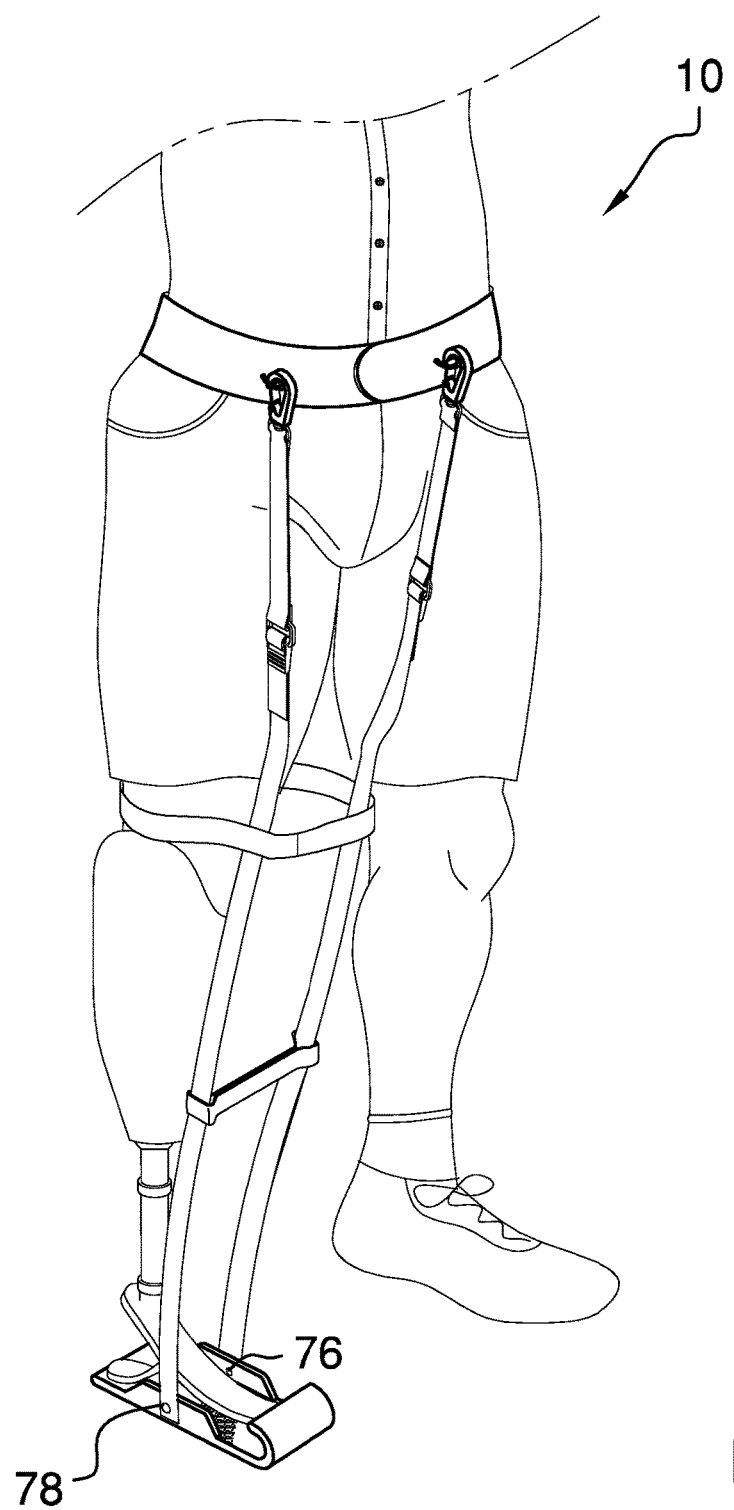
FIG. 7 is an in use view showing an expandable strap.

With reference now to the drawings, and in particular FIGS. 1 through 7 thereof, an example of the instant securing apparatus for a prosthetic leg employing the principles and concepts of the present securing apparatus for a prosthetic leg and generally designated by the reference number 10 will be described.

Referring to FIGS. 1 through 7 the present securing apparatus for a prosthetic leg 10 is illustrated. The securing apparatus for a prosthetic leg 10 includes a belt strap 20 having a right end 22, a left end 24, an interior surface 26, and an exterior surface 28. A pair of hook and loop fasteners 30 includes a hook fastener 32 and a loop fastener 34, with each of the hook fastener 32 and the loop fastener 34 disposed on the interior surface 26 of the belt strap 20 proximal the right end 22 and the exterior surface 28 of the belt strap 20 proximal the left end 24, respectively. The pair of hook and loop fasteners 30 is configured to selectively secure the right end 22 to the left end 24 around a waist of a user. A pair of top attachment loops 36 includes a right top attachment loop 38 and a left top attachment loop 40, with each of the right top attachment loop 38 and the left top attachment loop 40 having a pair of top ends 42 attached to the exterior surface 28 of the belt strap 20 proximal the right end 22 and the left end 24, respectively.

The securing apparatus for a prosthetic leg 10 further includes a sled-shaped support attachment 44. The support attachment 44 includes a substantially rectangular flattened base portion 46, a pair of substantially trapezoidal support extensions 48, and a pair of bottom attachment loops 50. The base portion 46 has a linear back edge 52, a right edge 54, a left edge 56, an upper surface 58, a lower surface 60, and an upwardly disposed convexly curved front area 62. A gripping member 64 is optionally disposed on the upper surface 58 of the base portion 46 of the support attachment 44. The pair of substantially trapezoidal support extensions 48 includes a right support extension 66 and a left support extension 68, with each of the right support extension 66 and the left support extension 68 having a top surface 70, an exterior side surface 72, and a bottom surface 74 medially disposed on the upper surface 58 of the base portion 46 adjacent to the right edge 54 and the left edge 56, respectively. Each of the pair of support extensions 48 is perpendicularly disposed to the base portion 46. The pair of bottom attachment loops 50 includes a right bottom attachment loop 76 and a left bottom attachment loop 78, with each of the right bottom attachment loop 76 and the left bottom attachment loop 78 having a pair of bottom ends 80 attached to the exterior side surface 72 of each of the right support extension 66 and the left support extension 68, respectively, proximal the top surface 70.

Each of a right ratchet strap 81 and a left ratchet strap 82 of a pair of ratchet straps 84 has an upper end 86, a lower end 88, a rearward facing upper spring-loaded clip 90 attached to the upper end 86, and a frontward facing lower spring-loaded clip 92 attached to the lower end 88. The upper spring-loaded clip 90 of each of the right ratchet strap 81 and the left ratchet strap 82 is removably attachable to the right top attachment loop 38 and the left top attachment loop 40, respectively. The lower spring-loaded clip 92 of each of the right ratchet strap 81 and the left ratchet strap 82 is removably attachable to the right bottom attachment loop 76 and the left bottom attachment loop 78, respectively, of the support attachment 44. Lastly, an expandable strap 94 has a right loop 96 and a left loop 98, with each of the right loop 96 and the left loop 98 slidably disposed around the right ratchet strap 81 and the left ratchet strap 82, respectively, proximal the lower end 88. The support attachment 44 selectively supports a foot portion 100 of a prosthetic leg 102 between the pair of support extensions 48 when the pair of ratchet straps 84 attaches the support attachment 44 to the belt strap 20.

The securing apparatus for a prosthetic leg 10 optionally includes a second top attachment loop 104 having a pair of second ends 106 attached to the exterior surface 28 of the belt strap 20 proximal the right top attachment loop 38. The right top attachment loop 38 is collinearly disposed between the hook fastener 32 and the second top attachment loop 104. The securing apparatus for a prosthetic leg 10 additionally optionally includes a support strap 108 having a securing mechanism 110. The securing mechanism 110 selectively secures the support strap 108 around the upper leg of the user and the pair of ratchet straps 84.

What is claimed is:

1. A securing apparatus for a prosthetic leg comprising:
a belt strap having a right end, a left end, an interior surface, and an exterior surface;
a pair of hook and loop fasteners comprising a hook fastener and a loop fastener, each of the hook fastener and the loop fastener disposed on the interior surface of the belt strap proximal the right end and the exterior surface of the belt strap proximal the left end, respectively, wherein the pair of hook and loop fasteners is configured to selectively secure the right end to the left end around a waist of a user;
a pair of top attachment loops comprising a right top attachment loop and a left top attachment loop, each of the right top attachment loop and the left top attachment loop having a pair of top ends attached to the exterior surface of the belt strap proximal the right end and the left end, respectively;
a sled-shaped support attachment further comprising:
a substantially rectangular flattened base portion having a linear back edge, a right edge, a left edge, an upper surface, a lower surface, and an upwardly disposed convexly curved front area;
a pair of substantially trapezoidal support extensions comprising a right support extension and a left support extension, each of the right support extension and the left support extension having a top surface, an exterior side surface, and a bottom surface medially disposed on the upper surface of the base portion adjacent to the right edge and the left edge, respectively;
wherein each of the pair of support extensions is perpendicularly disposed to the base portion; and
a pair of bottom attachment loops comprising a right bottom attachment loop and a left bottom attachment loop, each of the right bottom attachment loop and the left bottom attachment loop having a pair of bottom ends attached to the exterior side surface of each of the right support extension and the left support extension, respectively, proximal the top surface;
a pair of ratchet straps comprising a right ratchet strap and a left ratchet strap, each of the right ratchet strap and the left ratchet strap having an upper end, a lower end, a rearward facing upper spring-loaded clip attached to the upper end, and a frontward facing lower spring-loaded clip attached to the lower end;

wherein the upper spring-loaded clip of each of the right ratchet strap and the left ratchet strap is removably attachable to the right top attachment loop and the left top attachment loop, respectively;

wherein the lower spring-loaded clip of each of the right ratchet strap and the left ratchet strap is removably attachable to the right bottom attachment loop and the left bottom attachment loop, respectively, of the support attachment; and an expandable strap having a right loop and a left loop, wherein each of the right loop and the left loop is slidably disposed around the right ratchet strap and the left ratchet strap, respectively, proximal the lower end;

wherein the support attachment selectively supports a foot portion of a prosthetic leg between the pair of support extensions when the pair of ratchet straps attaches the support attachment to the belt strap.

2. The securing apparatus for a prosthetic leg of claim 1 further comprising second top attachment loop having a pair of second ends attached to the exterior surface of the belt strap proximal the right top attachment loop, wherein the right top attachment loop is collinearly disposed between the hook fastener and the second top attachment loop.

3. The securing apparatus for a prosthetic leg of claim 1 further comprising a support strap having a securing mechanism, wherein the securing mechanism selectively secures the support strap around the upper leg of the user and the pair of ratchet straps.

4. The securing apparatus for a prosthetic leg of claim 2 further comprising a support strap having a securing mechanism, wherein the securing mechanism selectively secures the support strap around the upper leg of the user and the pair of ratchet straps.

5. The securing apparatus for a prosthetic leg of claim 3 further comprising a gripping member disposed on the upper surface of the base portion of the support attachment.

6. The securing apparatus for a prosthetic leg of claim 4 further comprising a gripping member disposed on the upper surface of the base portion of the support attachment.

* * * * *